United States Patent [19]

Nakanishi

[11] Patent Number: 5,079,242
[45] Date of Patent: Jan. 7, 1992

[54] SUBSTITUTED 3-CEPHEM COMPOUNDS AS ANTIBACTERIAL AGENTS

[75] Inventor: Susumu Nakanishi, Niantic, Conn.

[73] Assignee: Pfizer Inc., New York, N.Y.

[21] Appl. No.: 460,117

[22] PCT Filed: Mar. 11, 1987

[86] PCT No.: PCT/US87/00531
  § 371 Date: Jul. 21, 1989
  § 102(e) Date: Jul. 21, 1989

[51] Int. Cl.$^5$ ............... C07D 501/20; A61K 31/545
[52] U.S. Cl. ............................... 514/202; 540/222; 540/226
[58] Field of Search ............ 540/222, 207, 225; 514/202, 206

[56] References Cited

U.S. PATENT DOCUMENTS

| | | | |
|---|---|---|---|
| 4,500,716 | 2/1985 | Kinast | 548/196 |
| 4,634,697 | 1/1987 | Hamashima | 514/202 |
| 4,647,658 | 3/1987 | Hamashima et al. | 540/215 |
| 4,912,212 | 3/1990 | Ochiai et al. | 540/227 |

FOREIGN PATENT DOCUMENTS

| | | |
|---|---|---|
| 82498 | 6/1983 | European Pat. Off. |
| 60-011490 | 1/1985 | Japan |
| 61-037788 | 2/1986 | Japan |

OTHER PUBLICATIONS

Chemical Abstracts 110:75164(e) (1989) Abstracting JP 63211287 dated Sep. 2, 1988, application 87/43,100 dated 2/27/87.

Primary Examiner—Nicholas S. Rizzo
Attorney, Agent, or Firm—Peter C. Richardson; J. Trevor Lumb; Mervin E. Brokke

[57] ABSTRACT

Certain 7-beta-[2-(2-amino-4-thiazolyl)-(Z)-2-(chloromethylene acetamido]-3-[(substituted)methyl]-ceph-3-em-4-carboxylic acids, pharmaceutically-acceptable salts thereof and conventional in vivo hydrolyzable esters thereof are valuable as broad spectrum antibacterial agents, particularly useful for the treatment of bacterial infections in man and other mammals.

16 Claims, No Drawings

SUBSTITUTED 3-CEPHEM COMPOUNDS AS ANTIBACTERIAL AGENTS

BACKGROUND OF THE INVENTION

The present invention is directed to certain 7-beta-[2-(2-amino-4-thiazolyl)-(Z)-2-(chloromethylene)acetamido]-3-[(substituted)methyl]ceph-3-em-4-carboxylic acids, pharmaceutically-acceptable salts thereof and conventional in vivo hydrolyzable esters thereof. These compounds are valuable as broad spectrum antibacterial agents, particularly useful for the systemic treatment of bacterial infections in man and other mammals; and, in the acid or salt form, as topical or industrial antibacterial agents.

The present invention employs a substantial number of the same 7-amino-3-(substituted)methyl]ceph-3-em-4-carboxylic acid precursors as those employed by Nagakura et al., published Japanese application 61-037788, in the synthesis of certain 7-beta-[D-2-((4-ethyl-2,3-dioxo-1-piperazino)carbonylamino)-alpha-2-(4-hydroxyphenyl)acetamido]-3-[(substituted)methyl]-3-cephem-4-carboxylic acids. Japanese published applications 58-164593 and 60-11490 describe 7-[2-(2-amino-4-thiazolyl)-2-(chloromethylene)acetamido]-3-methyl-ceph-3-em-4-carboxylic acid and a number of analogs substituted on 3-methyl with a variety of diaza- and polyaza-heteroarylthio groups.

SUMMARY OF THE INVENTION

The present invention is directed to antibacterial cephem compounds having the formula

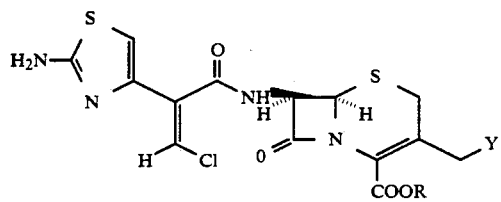

wherein
R is hydrogen or a radical forming a group which is hydrolyzable under physiological conditions;
Y is

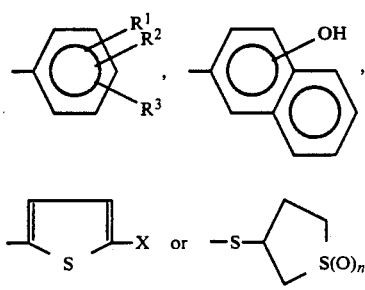

$R^1$ and $R^2$ are taken separately, and
$R^1$ is hydrogen, halogen, hydroxy, $(C_1-C_4)$-alkoxy or $(C_1-C_4)$alkyl, and
$R^2$ is hydrogen or $(C_1-C_4)$alkyl; or
$R^1$ and $R^2$ are taken together and attached to adjacent carbons, and form a methylenedioxo group;
$R^3$ is hydrogen or hydroxy; with the proviso that at least one of $R^1$, $R^2$ and $R^3$ is other than hydrogen, halogen or $(C_1-C_4)$alkyl;
X is hydrogen, halogen, $-CH_2COOH$, $-CH_2NH_2$ or $-CH_2NHCOR^4$;
$R^4$ is $(C_1-C_4)$alkanoyl or $(C_1-C_4)$alkanoyl substituted with halogen; and
n is 1 or 2;

a pharmaceutically-acceptable acid addition salt, or a pharmaceutically-acceptable cationic salt when R is hydrogen.

The term halogen, as used herein, refers to fluoro, chloro and bromo groups. Alkyl groups are straight chain or branched.

Pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluenesulfonic acid, 2-naphthalenesulfonic acid and methanesulfonic acid. Pharmaceutically-acceptable cationic salts include, but are not limited to, those of sodium, potassium, calcium, N,N'-dibenzylethylenediamine, N-methylglucamine (meglumine) and diethanolamine. The preferred cationic salts are those of potassium and sodium.

The reference to esters which are hydrolyzable under physiological conditions refers to those esters frequently referred to as in vivo hydrolyzable esters or "pro-drugs". Such esters are now as well-known and common in the penicillin art as pharmaceutically-acceptable salts. Such esters are generally used to enhance oral absorption, but in any event are readily hydrolyzed in vivo to the parent acid. The more preferred ester forming radicals are those wherein R is:
(5-methyl-1,3-dioxol-2-on-4-yl)methyl,
1H-isobenzofuran-3-on-1-yl,
gamma-butyrolacton-4-yl,
$-CHR^6OCOR^7$; or
$-CHR^6OCOOR^7$;
wherein $R^6$ is hydrogen or methyl; $R^7$ is $(C_1-C_6)$alkyl.
The most preferred radicals are pivaloyloxymethyl and 1-(ethoxycarbonyloxy)ethyl.

Because of their ease of preparation and excellent antibacterial activity, preferred compounds have Y as 3-fluoro-4-hydroxyphenyl, 3,4-dihydroxyphenyl, 3-carboxy-4-hydroxyphenyl, 5-chloro-2-thienyl, 5-(aminomethyl)-2-thienyl, 1,1-dioxo-3-thiolanylthio or cis-1-oxo-3-thiolanylthio.

The present invention is also directed to corresponding pharmaceutical compositions and a method of treating bacterial infections in mammals, including man.

DETAILED DESCRIPTION OF THE INVENTION

The present invention is readily carried out. The compounds of the formula (I) are best formed by coupling formylated side chain acid of the formula

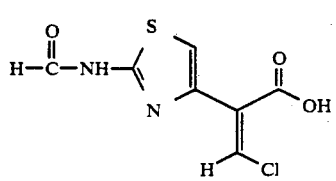

with a 7-aminocephem compound of the formula

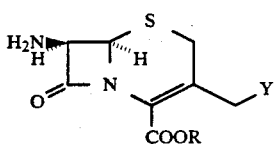

where R and Y are as defined above, to form an intermediate compound of the formula

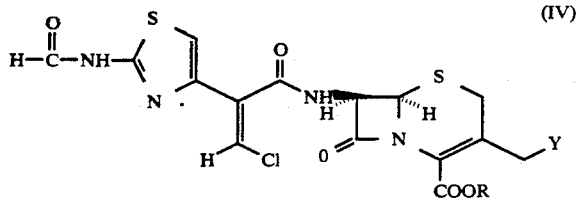

which, with or without isolation, is deformylated under mild solvolysis conditions to form the desired compound of the formula (I). When R is an ester group, said group can be already in place in the intermediate (IV) or alternatively introduced after coupling (and usually deformylation) have been accomplished.

The coupling step is accomplished by any one of a number of conventional methods well known in the beta-lactam and polypeptide arts. In the present invention, the preferred method employs a so-called Vilsmeier reagent, formed in situ from dimethylformamide and phosphorus oxychloride:

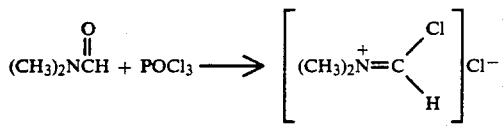

carried out in an anhydrous, aprotic, reaction-inert solvent, generally at a temperature below ambient, e.g., at about −25° to +10° C. The expression reaction-inert solvent, as used here and elsewhere herein refers to a solvent which does not interact with starting materials, reagents, intermediates or product in a manner which adversely affects the yield of the desired product. Methylene chloride is particularly well suited for this and subsequent stages of the present coupling process. Without isolation, the Vilsmeier reagent is then employed to activate the side chain acid, in the same solvent, but now generally at lower temperature, e.g., at about −15° to −30° C. When R is other than an ester forming radical, or the group Y contains a carboxylic acid function, the 7-aminocephem compound (III) is first protected as a silyl ester, conveniently using bis(-trimethylsilyl)acetamide as reagent. This will generally be done in the same reaction-inert solvent as that employed for activation of the side chain, usually at a temperature of about 5° to 35° C., ambient temperature being most convenient. The resulting solution is chilled and combined with the activated side chain, generally in the same temperature range employed to activate side chain, to form the intermediate N-formyl compound (IV), retaining any silyl ester protecting groups. The intermediate (IV) is optionally isolated, with facile removal of any silyl ester groups during the aqueous and/or alcoholic work-up. More convenient is to simply warm the coupling reaction to room temperature, dilute with methanol and allow deformylation to proceed in the resulting acid solution. If the intermediate (IV) is isolated, it is simply deformylated in acid methanol as a separate step.

The pharmaceutically-acceptable cationic salts of the present invention are readily prepared by standard methods. For example, an equivalent of the corresponding cationic hydroxide, carbonate or bicarbonate or of an amine, is combined with the carboxylic acid in an organic or aqueous solvent, preferably at reduced temperature (e.g., 0°-5° C.), with vigorous agitation and slow addition of the base. The salt is isolated by concentration and/or the addition of a non-solvent. The salt is alternatively isolated directly from a reaction mixture, i.e., without isolation of the free acid, otherwise using similar techniques.

Likewise pharmaceutically-acceptable acid addition salts of the present invention are readily prepared by standard methods. For example, an equivalent of the acid is combined with the free amine form of the compound in an organic or aqueous organic solvent. The salt is isolated by concentration and/or the addition of a non-solvent. The salt is alternatively isolated directly from a reaction mixture, i.e., without isolation of the free amine, otherwise using similar techniques.

The compounds of the formula (I) wherein R represents a radical forming an in vivo hydrolyzable ester are prepared from the corresponding free acids or cationic salts according to known methods, readily identified by those skilled in the penicillin art (see for example U.S. Pat. Nos. 3,951,954; 4,234,579; 4,287,181; 4,342,693; 4,452,796; 4,342,693; 4,348,264; 4,416,891; and 4,457,924). Methods of preparation are exemplified below. If desired, an ester containing a basic amine or carboxylic acid function is converted to an acid addition salt or cationic salt, respectively, according to the methods of the immediately preceding paragraphs.

The required starting materials of the formulas (II) and (III) are prepared from known and available materials according to the preparative methods which are specifically exemplified below.

As indicated above, the compounds of the formula (I) are useful as antibacterial agents. Such activity is demonstrated in vitro by measuring the minimum inhibitory concentrations (MIC's) in mcg/ml against a variety of microorganisms for those compounds where R is hydrogen. The procedure which is followed is the one recommended by the International Collaborative Study on Antibiotic Sensitivity Testing (Ericcson and Sherris, Acta. Pathologica et Microbiologia Scandinav, Supp 217, Section B: 64–68 [1971]), and employs brain heat infusion (BHI) agar and an inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye. Such measurements on the compounds (I) wherein R is hydrogen are, of course, determinative of the inherent antibacterial activity of those compounds where R forms a conventional in vivo hydrolyzable ester.

Those compounds of the formula (I) having said in vitro antibacterial activity are thus useful as industrial antimicrobials, for example in water treatment, slime control, paint preservation and wood preservation, as well as for topical application in mammals. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

In determining such in vivo activity of the compounds of the formula (I), acute experimental infections are produced in mice by the intraperitoneal inoculation of the mice with a standardized culture of the test organism suspended in 5 percent hog gastric mucin. Infection severity is standardized so that the mice receive a lethal dose of the organism (the lethal dose is the minimum inoculum of organism required to consistently kill 100 percent of the infected, non-treated control mice). The test compound of the formula (I) is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as $PD_{50}$ (dose which protects 50% of the animals from infection). Preferred for oral (p.o.) use are those compounds of the formula (I) wherein R represents an in vivo hydrolyzable ester; while for parenteral (i.p.) use, those compounds wherein R is hydrogen are preferred.

When using one of the present antibacterial compounds of the formula (I) for systemic control of bacterial infections in a mammal, particularly man, the compound is administered alone, or mixed with pharmaceutically acceptable carriers or diluents, in the form of unit dosage forms for oral or parenteral use. For oral use, in vivo hydrolyzable esters are generally preferred, while for parenteral use (e.g., i.m. or i.v.), acid or salt forms are generally preferred. The daily dosage will be similar to those of other clinically useful beta-lactam antibiotics. Although the prescribing physician will ultimately decide the dosage to be used in a human subject, these compounds will normally be used orally at dosages in the range from about 20 to about 100 mg. per kilogram of body weight per day, and parenterally at dosages from about 10 to about 100 mg. per kilogram of body weight per day, usually in divided doses. In some instances, the prescribing physician will determine that dosages outside these limits are needed.

For oral administration, tablets, capsules, lozenges, troches, powders, syrups, elixirs, aqueous solutions and suspension, and the like are used, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying or suspending agents. If desired, certain sweetening and/or flavoring agents can be added. For parenteral administration, which includes intramuscular, intraperitoneal, subcutaneous, and intravenous injection, sterile solutions of the active ingredient are usually prepared, and the pH of the solutions are suitably adjusted and buffered. For intravenous use, the total concentration of solutes should be controlled to render the preparation isotonic The present invention is illustrated by the following examples. However, it should be understood that the invention is not limited to the specific details of these examples.

EXAMPLE 1

Step 1

7-beta-[2-(2-Formylamino-4-thiazolyl)-(Z)-2-(chloromethylene)acetamido-3-[(3-fluoro-4-hydroxyhydroxyphenyl)methyl]ceph-3-em-4-carboxylic Acid Under nitrogen, 12.7 ml of methylene chloride and 2.2 ml of anhydrous dimethylacetamide were cooled with stirring to 0° C. $POCl_3$ (1.58 ml, 2.64 g, 17.2 mmols) was added, the mixture stirred at 0° C. for 30 minutes and then cooled to −20° to −23° C., and finally 2-(2-formylamino-4-thiazolyl)-(Z)-2-(chloromethylene)acetic acid (2.09 g, 9 mmols) was added in 4 portions. The reaction mixture was maintained at −20° to −23° C. while in a separate flask also under nitrogen, 7-beta-amino-3-[(3-fluoro-4-hydroxyphenyl)methyl]-ceph-3-em-4-carboxylic acid (2.5 g, 7.7 mmols) was suspended in 25 ml of $CH_2Cl_2$ at room temperature, and 6.65 ml of bis(trimethylsilyl)acetamide (BSA) added. The resulting clear solution was stirred for 1 hour at room temperature and then added to the cold reaction mixture and reacted at −20° to −23° C. for 1 hour. The reaction was quenched by the addition of 60 ml of methanol and concentrated to an oily residue, which was distributed between 350 ml ethyl acetate and 175 ml $H_2O$, with the pH adjusted to 2.5 by the addition of saturated $NaHCO_3$. The organic layer was separated, washed with 100 ml of water, dried over anhydrous sodium sulfate and evaporated to dryness to give title product as a solid 2.68 g, used directly in Step 2.

Step 2

7-beta-[2(2-Amino-4-thiazolyl)-(Z)-2-(chloromethylene)acetamido]-3-[(3-fluoro-4-hydroxyphenyl)-methyl]ceph-3-em-4-carboxylic Acid Crude formyl product prepared according to Step 1 (2.93 g) was dissolved in 100 ml of methanol, 1.5 ml (18 mmols) of concentrated HCl added, and the mixture stirred at room temperature for 3 hours, then held 18 hours at 4° to 5° C., at which time $H_2O$ (120 ml) was added and the mixture concentrated to ½ volume. The pH of the resulting slurry was made 7 by the addition of saturated $NaHCO_3$ and the resulting solution clarified by filtration. The pH of the filtrate was adjusted to 3.5 by the addition of 6N HCl and 1N HCl. Solid was collected by a filtration, washed with water and dried to give 1.44 g of crude product. Purification was achieved by suspending the crude product (1.2 g) in 30 ml of water, adjusting the pH to 8.2 with saturated $NaHCO_3$, and extracting with 20 ml of ethyl acetate. The aqueous layer was separated, the pH readjusted to 3.5 with 1N HCl and purified title product collected by filtration, washed with water and dried in vacuo overnight. Yield: 760 mg; m.p. 189°-190° C.(dec.); ir (KBr) 3316, 1764, 1629, 1514, 1439, 1364, 1290, 1237, 1183, 1112, 1060, 1011, 952, 900, 816, 791, 728, 582, 204 cm$^{-1}$. Nmr (DMSO-d$_6$) 5.05 (d, C$_6$-H), 5.63 (q, C$_7$-H).

EXAMPLE 2

7-beta-[2-(2-Amino-4-thiazolyl)-(Z)-2-(chloromethylene)acetamido]-3-[(5-chloro-2-thienyl)-methyl]-ceph-3-em-4-carboxylic Acid Under nitrogen, 1.27 ml of CH$_2$Cl$_2$ and 0.22 ml of anhydrous dimethylacetamide was cooled to 0° C. POCl$_3$ (0.213 ml) was added, and the mixture stirred at 0° C. for 30 minutes, then cooled to −20° to −23° C. 2-(2-Formylamino-4-thiazolyl)-(Z)-2-(chloromethylene)acetic acid (272 mg) was added and the mixture stirred for 10 minutes at −20° to −23° C. Meanwhile, in a separate flask, 7-beta-amino-3-[(5-chloro-2-thienyl)-methyl]ceph-3-em-4-carboxylic acid (330.8 mg) was suspended in 2.5 ml of methylene chloride at room temperature, 0.863 ml of bis(trimethylsilyl)acetamide (BSA) was added, and the resulting solution stirred at room temperature for 1 hour, added to the cold reaction mixture at −20° to −23° C. and reacted at that temperature for 1 hour. The mixture was warmed up to room temperature, 6 ml of methanol was added, and the mixture was stirred at room temperature for 2 hours to complete deformylation. Finally, the reaction mixture was concentrated to an oily residue which was dissolved in 10 ml of ethyl acetate and 5 ml of water. The pH of the mixture was adjusted to 7.5 with saturated NaHCO$_3$. The aqueous layer was separated, filtered, and the pH of the filtrate was adjusted to 3.0 by an addition of 6N and 1N HCl. The mixture was filtered, the solids washed well with water and dried overnight in vacuo to yield title product, 140 mg; m.p. 184°-185° (dec.).

EXAMPLE 3

Step 1

7-beta-[2-(2-Formylamino-4-thiazolyl)-(Z)-2-(chloromethylene)acetamido]-3-[(1,1-dioxo-3-thiolanylthio)methyl]ceph-3-em-4-carboxylic Acid By the method of Step 1 of Example 1, 7-beta-amino-3-[(1,1-dioxo-3-thiolanylthio)methyl]ceph-3-em-4-carboxylic acid (312 mg, 0.85 mmol) was converted to crude, partially deformylated title product, 179 mg.

Step 2

7-beta-[2-(2-Amino-4-thiazolyl)-(Z)-2-(chloromethylene)acetamido]-3-[(1,1-dioxo-3-thiolanylthio)methyl]ceph-3-em.-4-carboxylic Acid By the method of Step 2 of Example 1, present Step 1 product (170 mg) was converted to present title product, 104 mg; ir (KBr) 1774, 1665, 1630 cm$^{-1}$; $^1$H-nmr (DMSO-d$_6$) includes 9.6(m), 7.16 (broad s), 6.83 (s), 6.40 (s), 5.74 (dd), 5.2 (d), 3.8-2.8 (unresolved multiplets), 1.96 (m).

EXAMPLE 4

7-beta-[2-(2-Amino-4-thiazolyl)-(Z)-2-(chloromethylene)acetamido]-3-[(cis-1-oxo-3-thiolanylthio)methyl]ceph-3-em-4-carboxylic Acid By the method of Example 2, 7-beta-amino-3-[(cis-1-oxo-3-thiolanylthio)methyl]ceph-3-em-4-carboxylic acid (321 mg, 0.92 mmol) was converted to present title product, 79 mg; ir (KBr) 1772, 1659, 1634 cm$^{-1}$; $^1$H-nmr (DMSO-d$_6$) 9.6 (m, 1H) 7.15 (broad s, 2H), 6.83 (s, 1H), 6.34 (s, 1H), 5.73 (dd, 1H), 5.21 (d, 1H), 3.8-1.7 (unresolved multiplets).

EXAMPLE 5

7-beta-[2-(2-Amino-4-thiazolyl)-(Z)-2-(chloromethylene)acetamido]-3-[(3-carboxy-4-hydroxyphenyl)-methyl]ceph-3-em-4-carboxylic Acid By the method of Example 2, 7-beta-amino-3-[(3-carboxy-4-hydroxyphenyl)methyl]-3-cephem-4-carboxylic acid (0.35 g, 1 mmol) was converted to title product 315 mg, m.p. 235°-237° C. (dec.); ir (KBr) 3367, 1774, 1661, 1544, 1489, 1442, 1366, 1244 cm$^{-1}$; $^1$H-nmr (DMSO-d$_6$) 3.1-4.2 (m), 4.9 (d), 5.05 (d), 5.2 (d), 5.8 (q), 6.4 (s), 6.8 (q), 7.1-7.4 (m), 7.6 (q), 9.6 (d).

EXAMPLE 6

7-beta-[2-(2-Amino-4-thiazolyl-(Z)-2-(chloromethylene)acetamido]-3-[(3,4-dihydroxyphenyl)methyl]-ceph-3-em-4-carboxylic Acid By the method of Example 2, 7-beta-amino-3-[(3,4-dihydroxyphenyl)methyl]ceph-3-em-4-carboxylic acid (306 mg, 1 mmol) was converted to present title product, 407 mg; $^1$H-nmr (DMSO-d$_6$) 3.4-3.6 (m), 5.2 (d), 5.6-5.8 (dd), 6.4-6.8 (q), 7.1 (s), 8.75 (d), 9.6 (d).

EXAMPLE 7

7-beta-[2-(2-Amino-4-thiazolyl)-(Z)-2-methylene)acetamido]-3-[(5-(2-chloroacetamidomethyl)-2-thienyl)methyl]-ceph-3-em-4-carboxylic Acid By the method of Example 2, 7-beta-amino-3-[(5-(chloroacetylaminomethyl)thienylmethyl]-ceph-3-em-4-carboxylic acid (0.802 g) was converted to present title product, 658 mg; m.p. 152°-155° C.; ir (KBr) 3293, 3066,, 2954, 1765, 1657, 1366, 1232, 1182, 1058, 1038 cm$^{-1}$; $^1$H-nmr (DMSO-d$_6$) 3.2-3.6 (m, CH$_2$), 4.07 (s, 2H), 4.37 (d, CH$_2$), 5.17 (d, C$_6$-H), 5.7 (q, C$_7$-H), 6.8 (d), 7.1 (s), 8.8 (q), 9.5 (d).

EXAMPLE 8

7-beta-[2-(2-Amino-4-thiazolyl)-(Z)-2-(chloromethylene)acetamido]-3-[5-(aminomethyl)-2-thienyl)methyl]ceph-3-em-4-carboxylic Acid Title product of the preceding Example (640 gm) was suspended in a mixture of 6.5 ml of CH$_3$CN and 3.2 ml of water. Thiourea (246 mg) and 220 mg of sodium acetate trihydrate were added, and the mixture was stirred at room temperature for 18 hours, at which time 50 ml of isopropyl alcohol was added dropwise. The resulting solids were filtered, washed well with isopropyl alcohol and dried in vacuo overnight to yield 400 mg of the title product, m.p. 185°-187° (dec.), solvated with one molar equivalent of isopropyl alcohol (by nmr). The latter was suspended in a mixture of 20 ml of ethyl acetate and 10 ml of water and the pH was made 2 by the addition of 1N HCl. The aqueous layer was separated and the pH adjusted to 3.1 with saturated NaHCO$_3$. The resulting solid was collected by filtration, washed well with water and dried in vacuo overnight to yield title product, 90 mg; m.p. 197°-198° C. (dec.); ir (KBr) 3300, 3062, 1762, 1651, 1528, 1389, 1365, 1281, 1231, 1184, 1056, 1016 cm$^{-1}$; $^1$H-nmr (DMSO-d$_6$) 3.2-3.6 (m), 3.9 (s), 4.4 (d), 5.06 (d, C$_6$-H), 5.66 (s, C$_7$-H), 6.39 (s), 6.7 (q), 7.18 (s), 9.0 (q), 9.5 (d).

EXAMPLE 9

Pivaloyloxymethyl
7-beta-[2-(2-amino-4-thiazolyl)-(Z)-2-(chloromethylene)acetamido]-3-[(3-fluoro-4-hydroxyphenyl)methyl]ceph-3-em-4-carboxylate Title product of Example 1 (300 mg) in 1.5 ml anhydrous dimethylacetamide was combined with triethylamine (0.164 ml) and chloromethyl pivalate (0.17 ml) and reacted for 18 hours at room temperature. The reaction mixture was diluted with 2.5 ml H$_2$O, extracted 2×4 ml ethyl acetate, and the extracts combined, backwashed with 2.5 ml H$_2$O, dried over MgSO$_4$ and evaporated to dryness. The resulting residue (300 mg) was triturated and stirred with 4 ml ether, filtered and dried in vacuo to yield title product, 125 mg; ir (KBr) 1780, 1755, 1665 cm$^{-1}$; $^1$H-nmr (DMSO-d$_6$) 1.16 (s, 9H), 2.05 (s, 3H), 3.2–4.0 (m), 5.6–6.2 (m), 6.86 (s, 1H), 7.10 (dd), 9.55 (d).

By the substitution of an equivalent amount of alpha-chloroethyl ethyl carbonate for chloromethylpivalate, this method is used to produce 1-(ethoxycarbonyloxy)ethyl 7-beta-[2-(2-amino-4-thiazolyl)-(Z)-2-(chloromethylene)acetamido]-3-[(3-fluoro-4-hydroxyphenyl)methyl]ceph-3-em-4-carboxylate.

By the substitution of an equivalent amount of the title product of Example 4 for the title product of Example 1, this method is used to produce pivaloyloxymethyl 7-beta-[2-(2-amino-4-thiazolyl)-(Z)-2-(chloromethylene)acetamido]-3-[(cis-1-oxo-3-thiolanylthio)methyl]ceph-3-em-4-carboxylate. In like manner, the corresponding 1-(ethoxycarbonyloxy)ethyl ester is prepared by further substituting alpha-chloroethyl ethyl carbonate for chloromethylpivalate.

PREPARATION 1

Ethyl 2-Formyl-2-(2-formylamino-4-thiazolyl)acetate

Under nitrogen, 14 g (0.29 mmol) of 50% NaH in oil was washed with 2×40 ml of hexane and then suspended in 90 ml of anhydrous tetrahydrofuran (THF). To this slurry at 0° C. was added dropwise a solution of ethyl 2-(2-amino-4-thiazolyl)acetate (27 g, 0.145 mmol) in 290 ml of anhydrous THF, followed by ethyl formate (21.5 g, 0.29 mmol), and the mixture stirred at room temperature for 18 hours. The pH of reaction mixture was adjusted to 7 by the addition of 50% aqueous acetic acid and the mixture extracted with 250 ml ethyl acetate. The aqueous layer was further extracted with 2×50 ml of 1:1 THF:ethyl acetate. The extracts were combined, dried over Na$_2$SO$_4$ and evaporated to a solid, which was recrystallized from ethyl acetate to yield purified title product, 17.8 g (50.7%); m.p. 179°–180° C.; $^1$H-nmr (CDCl$_3$-d$_6$-DMSO) 1.33 (t, 3H), 4.16 (q, 2H), 7.50 (s, 1H), 8.00 (s, 1H), 8.53 (s, 1H).

PREPARATION 2

Ethyl 2-(Chloromethylene)-2-[2-(dimethylaminomethyleneamino)-4-thiazolyl]acetate Title product of the preceding Preparation (20 g, 82 mmols) was dissolved in 100 ml of dimethylformamide. With tap water cooling, 15.6 g (100 mmols) of POCl$_3$ was added in 4 portions. The stirred mixture was reacted at 100°±2° C. for 1.5 hours, cooled to room temperature, the pH adjusted to 7 with 6N NaOH and 1N NaOH and extracted with 2×150 ml ethyl acetate. The combined organic extracts were dried over Na$_2$SO$_4$, evaporated to yield title product as an oil (26.23 g), which consisted of a mixture of syn- and anti-isomers.

PREPARATION 3

Ethyl (Z)-2-(chloromethylene)-2-(2-formylamino-4-thiazolyl)acetate

To the title product of the preceding Preparation (26 g) was added 52.3 ml of acetic formic anhydride reagent (Fieser and Fieser Reagents for Org. Syn. Vol. 1, page 4) and the mixture stirred at room temperature for 4 hours. Water (200 ml) was added and the mixture concentrated in vacuo to an oil. The oil was taken up in 200 ml ethyl acetate, washed 1×100 ml saturated NaHCO$_3$ and 1×100 ml water, dried over Na$_2$SO$_4$ and evaporated to dryness to give 20.24 g of solid, a mixture of syn- and anti-isomers. To separate the desired (Z)-isomer, the mixture (20 g) was dissolved by warming in the minimum necessary CHCl$_3$ and chromatographed on 1 kg of silica gel with 5:1 CHCl$_3$:ethyl acetate as eluant to yield purified title product, 12.17 g, m.p. 97°–99° C.

PREPARATION 4

(Z)-2-(Chloromethylene)-2-(2-formylamino-4-thiazolyl)acetic Acid

The title product of the preceding Example (5.21 g, 20 mmols) was suspended in 11 ml of tetrahydrofuran and cooled to 0° C., 3.37 g (60 mmols) of KOH in 55 ml of water was added dropwise at 0° C., and the resulting mixture stirred at room temperature for 7 hours, then extracted with 2×55 ml of 1:1 ethyl acetate:diethyl ether. The residual aqueous layer was cooled to 0° C., and the pH adjusted to 2.0 with 6N HCl and 1N HCl. The solid was collected by a filtration, washed with water and dried overnight to give crude title product 3.93 g (85%), m.p. 144°–145° (dec.) contaminated with free amine. This crude was re-formylation by a treatment with 21 ml of acetic-formic anhydride at room temperature for 4 hours, concentrated under in vacuo, and the solid residue slurried in hexane, filtered and dried overnight in vacuo to yield 4 g of purified title product, m.p. 151°–152° C. (dec.).

PREPARATION 5

7-beta-Amino-3-[(3-fluoro-4-hydroxyphenyl)-methyl]-ceph-3-em-4-carboxylic Acid

7-Aminocephalosporanic acid (7-ACA, 7-beta-amino-3-(acetoxymethyl)ceph-3-em-4-carboxylic acid; 5.44 g, 20 mmols) was dissolved in 40 ml of trifluoroacetic acid at 10° to 15° C. To the stirred solution was added borontrifluoride etherate (11.35 g, 80 mmols) followed by 3.36 g (30 mmols) of 2-fluorophenol, maintaining 10° to 15° C. throughout both additions. The resulting mixture was stirred at 23° to 25° C. for 4.5 hours, then concentrated in vacuo to an oily solid which was dissolved in 30 ml of water. The resulting solution was cooled in ice-bath and the pH adjusted to 3.5 by a dropwise addition of 28% NH$_4$OH. The resulting solids were collected by a filtration, washed well with water, dried in vacuo overnight to yield title product, 6.35 g (98%), m.p. 170°–171° C.; ir (KBr) 1798, 1674, 1616, 1514, 1474 cm$^{-1}$; $^1$H-nmr (DMSO-d$_6$) 9.63 (s, 1H), 6.6–7.2 (m, 3H), 4.87 (d, 1H), 4.66 (d, 1H), 3.02–3.68 (m, 6H).

By the same method, substituting a molar equivalent of the appropriate phenol, aryl ether or thiophene for 2-fluorophenol, the following additional compounds were prepared:

7-beta-Amino-3-[(3,5-di(t-butyl)-4-hydroxyphenyl)methyl]ceph-3-em-4-carboxylic acid; 33% yield; ir (KBr) 1770 cm$^{-1}$; $^1$H-nmr (DMSO-d$_6$) 1.37 (s, C(CH$_3$)$_3$), 3.0–4.5 (m, 3H), 4.72 (d, J=4,6Hz, 1H), 4.99 (d, J=4.6Hz, 1H), 7.06 (2H).

7-beta-Amino-3-[(3,4-dihydroxyphenyl)methyl]-2-ceph-3-em-4-carboxylic acid; 61% yield; ir (KBr) 1770 cm$^{-1}$; $^1$H-nmr (DMSO-d$_6$) 2.80–4.20 (m, 3H), 4.73 (d, J=5.0Hz, 1H), 5.00 (d, J=5.0Hz), 6.4–7.00 (m, 3H).

7-beta-Amino-3-[(3,5-dimethyl-4-hydroxyphenyl)methyl]ceph-3-em-4-carboxylic acid; 89% yield; ir (KBr) 1800 cm$^{-1}$; $^1$H-nmr (DMSO-d$_6$) 2.15 (s, aryl CH$_3$, 6H), 3.12/3.46 (dd, J=17Hz, C$_3$-CH$_2$), 3.46/3.76 (dd, J=14.6Hz), C$_2$-H$_2$, 4.74/4.76 (d, J=4.5, C$_7$-H and C$_8$-H), 6.83 (aryl H).

7-beta-Amino-3-[(2,4-dihydroxyphenyl)methyl]ceph-3-em-4-carboxylic acid; 33% yield; ir (KBr) 1770 cm$^{-1}$; $^1$H-nmr (DMSO-d$_6$) 2.80–4.40 (m-C$_2$H$_2$, C$_3$-CH$_2$), 4.75/4.95 (2d, J=5.0Hz, C$_7$-H and C$_8$-H), 6.05–7.05 (m, aromatic-H).

7-beta-Amino-3-[(2,5-dihydroxyphenyl)methyl]ceph-3-em-4-carboxylic acid; 53% yield; ir (KBr) 1770 cm$^{-1}$; $^1$H-nmr (DMSO-d$_6$) 3.00–4.00 (m, C$_2$-H$_2$, C$_3$-CH$_2$), 4.75/5.02 (2d, J=5.0Hz, C$_7$-H and C$_8$-H), 6.40–7.00 (m, aromatic H).

7-beta-Amino-3-[(3-carboxy-4-hydroxyphenyl)methyl]ceph-3-em-4-carboxylic acid; 57% yield; ir (KBr) 3509, 1801 cm$^{-1}$; $^1$H-nmr (DMSO-d$_6$) 7.7 (q, 1H), 7.41 (q, 1H), 6.8 (m, 3H), 3.3–5.1 (m, 6H), 2.0 (s, 1H).

7-beta-Amino-3-[(4-hydroxy-2-naphthyl)methyl]ceph-3-em-4-carboxylic acid; 81% yield; ir (KBr) 1780 cm$^{-1}$; $^1$H-nmr (DMSO-d$_6$) 3.10–3.60 (m, C$_3$-CH$_2$), 4.00–4.30 (s, C$_2$-H), 6.70–8.40 (m, aromatic H).

7-beta-Amino-3-[(4-methoxyphenyl)methyl]ceph-3-em-4-carboxylic acid; 69% yield; ir (KBr) 1800, 1245 cm$^{-1}$; $^1$H-nmr (DMSO-d$_6$) 3.10–3.50 (dd, J=17.2Hz), C$_3$-CH$_2$), 3.75 (s, OCH$_3$), 3.50–4.10 (m, C$_2$-H), 4.73/5.00 (2d, J=5.0Hz, C$_7$-H and C$_8$-H), 6.89–7.22 (dd, J=9.0Hz, aromatic H).

7-beta-Amino-3-[(3,4-methylenedioxyphenyl)methyl]ceph-3-em-4-carboxylic acid; 74% yield; ir (KBr) 1795, 1225 cm$^{-1}$; $^1$H-nmr (DMSO-d$_6$); 3.12-3.52 (dd, J=17Hz, C$_3$-CH$_2$), 3.45–3.87 (dd, J=16Hz, C$_2$H), 4.75/5.03 (2d, J=5.0Hz, C$_7$-H), 6.01 (s, —OCH$_2$O), 6.60–7.10 (m, aromatic H).

7-beta-Amino-3-[3,4-dihydroxy-5-methoxyphenyl)methyl]ceph-3-em-4-carboxylic acid; 63% yield; ir (KBr) 1780 cm$^{-1}$; $^1$H-nmr (DMSO-d$_6$) 3.00–4.10 (m, C$_2$H, C$_3$-CH$_2$), 3.70 (s, OCH$_3$), 4.72/4.96 (2d, J=5.0Hz, C$_7$-H and C$_8$-H), 6.30–6.70 (m, aromatic H).

7-beta-Amino-3-[(4-hydroxy-3,5-dimethoxyphenyl)methyl)ceph-3-em-4-carboxylic acid; 99% yield; ir (KBr) 1795 cm$^{-1}$; $^1$H-nmr (DMSO-d$_6$), 3.0–4.10 (m, C$_2$-H, C$_3$-CH$_2$), 3.72 (s, OCH$_3$), 3.80 (s, OCH$_3$), 4.75/4.97 (2d, J=5.0Hz, C$_7$-H and C$_8$-H), 6.68 (s, aromatic H).

7-beta-Amino-3-(2-thienylmethyl)ceph-3-em-4-carboxylic acid; 85% yield; ir (KBr) 1790 cm$^{-1}$; $^1$H-nmr (DMSO-d$_6$) 3.20, 3.61 (dd, J=17Hz, C$_3$-CH$_2$), 3.50–4.20 (m, C$_2$-H), 4.75/5.01 (2d, J=5Hz, C$_7$-H and C$_8$-H), 6.60–7.60 (m, heteroaromatic hydrogen).

7-beta-Amino-3-[(5-bromo-2-thienyl)methyl]ceph-3-em-4-carboxylic acid; 39% yield; ir (KBr) 1800 cm$^{-1}$; $^1$H-nmr (DMSO-d$_6$) 3.21, 3.65 (dd, J=17Hz, C$_3$CH$_2$), 3.68, 4.05 (dd, J=15Hz, C$_2$-H), 4.75 (d, J=5Hz), 5.00 (d, J=5.0Hz), 6.85–7.08 (dd, J=3.6Hz, heteroaromatic H).

7-beta-Amino-3-[(5-(carboxymethyl)-2-thienyl)methyl]ceph-3-em-4-carboxylic acid; 77% yield; ir (KBr) 1800, 1710 cm$^{-1}$; $^1$H-nmr (DMSO-d$_6$) 3.23–3.62 (dd, J=17Hz, C$_3$-CH$_2$), 3.68–4:05 (dd, J=16Hz, C$_2$-H), 3.75 (s, —CH$_2$COOH), 4.73 (d, J=5Hz), 5.00 (d, J=5Hz), 6.80 (s, heteroaromatic H).

7-beta-Amino-3-[(5-(2-chloroacetylamino)methyl-2-thienyl)methyl]ceph-3-em-4-carboxylic acid; 99% yield; ir (KBr) 1800, 1650 cm$^{-1}$; 1H-nmr (DMSO-d$_6$) 3.25–3.60 (dd, J=17Hz, C$_3$-CH$_2$), 3.68–4.02 (dd, J=15Hz, C$_2$-H), 4.10 (s, COCH$_2$Cl), 4.40 (d, J=5.5Hz, —CH$_2$NH—), 4.75 (d, J=5Hz), 5.00 (d, J=5Hz), 6.81 (s, heteroaromatic H), 8.78 (broad, —NHCO—).

7-beta-Amino-3-[(5-chloro-2-thienyl)methyl]ceph-3-em-4-carboxylic acid; 96% yield; m.p. 188°–190° C. (dec.); ir (KBr) 1800, 1620, 795 cm$^{-1}$; $^1$H-nmr (DMSO-d$_6$) 6.9 (d, 1H), 6.8 (d, 1H$_{0, 4.9}$(d, 1H0, 4.7 (d, 1H), 3.9 (d, 1H), 3.5–3.6 (q, 4H), 3.2 (d, 1H).

7-beta-Amino-3-[(4- and 2-hydroxyphenyl)methyl]-ceph-3-em-4-carboxylic acid; 87% yield (o, p mixture); ir (KBr) 1780 cm$^{-1}$; $^1$H-nmr (DMSO-d$_6$) 3.06–3.51 (dd, J=18Hz, C$_3$-CH$_2$), 3.41–3.80 (dd, J=14Hz, C$_2$H), 4.72–4.99 (d, J=5Hz, C$_7$-H, C$_8$-H), 6.70–7.08 (q, J=8Hz, aromatic H).

PREPARATION 6

7-beta-A is-(1-oxo-3-thiolanylthio)methyl]ceph-3-em-4-carboxylic acid

Under nitrogen, anhydrous acetonitrile (1.4 ml) was cooled to 5° C., 8 ml of BF$_3$OEt$_2$ was added and the mixture stirred at 5°–10° C. for 30 minutes. Maintaining the same temperature range, cis-3-mercaptothiolane-1-oxide (806 mg) in 2.8 ml acetonitrile was added, followed by 7-ACA (942 mg) in portions. The temperature was increased and the mixture stirred 5 hours at room temperature, then poured into 40 ml of water and ice, the pH adjusted to 3.5, and title product recovered by filtration, washed well with water, and dried to yield 1.1 g (91%) of title product; ir (KBr) 1800, 1620 cm$^{-1}$; $^1$H-nmr (DMSO-d$_6$) 5.02 (d, 1H), 4.76 (d, 1H), 3.45–3.81 (m), 2.2–2.9 (m).

By the same method, 3-mercaptothiolane-1,1-dioxide was converted to 7-beta-amino-3-[(1,1-dioxo-3-thiolanylthio)methyl]ceph-3-em-4-carboxylic acid in 90% yield; m.p. 206°–208° C. (dec.); ir (KBr) 1803, 1619, 1170 cm$^{-1}$; 1H-nmr (DMSO-d$_6$) 4.99 (2d, J=4.8Hz, 1H, reflecting racemic side), 4.73 (d, J=4.8Hz, 1H), 3.8–2.8 (unresolved multiplet), 2.41 (m, 1H), 1.94 (m, 1H).

What is claimed is:
1. A cephem having the formula

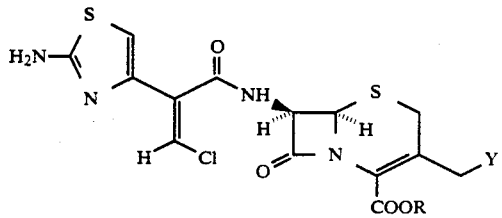

wherein

R is hydrogen or a radical forming a group which is hydrolyzable under physiological conditions;
Y is

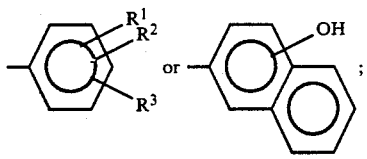

$R^1$ and $R^2$ are taken separately, and
  $R^1$ is hydrogen, halogen, hydroxy, $(C_1-C_4)$alkoxy or $(C_1-C_4)$ alkyl, and
  $R^2$ is hydrogen or $(C_1-C_4)$alkyl; or
$R^1$ and $R^2$ are taken together and attached to adjacent carbons, and form a methylenedioxo group;
$R^3$ is hydrogen or hydroxy; with the proviso that at least one of $R^1$, $R^2$ and $R^3$ is other than hydrogen, halogen or $(C_1-C_4)$alkyl; and
$R^4$ is $(C_1-C_4)$alkanoyl or $(C_1-C_4)$alkanoyl substituted with halogen;
a pharmaceutically-acceptable acid addition salt, or a pharmaceutically-acceptable cationic salt when R is hydrogen.

2. A cephem of claim 1 wherein R is hydrogen.
3. A cephem of claim 2 wherein Y is

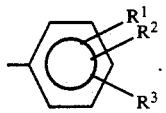

4. The cephem of claim 3 wherein Y is

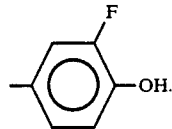

5. The cephem of claim 3 wherein Y is

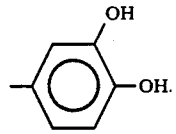

6. The cephem of claim 3 wherein Y is

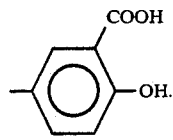

7. A cephem of claim 1 wherein R is:
(5-methyl-1,3-dioxol-2-on-4-yl)methyl,
1H-isobenzofuran-3-on-1-yl,
gamma-butyrolacton-4-yl,
—$CHR^6OCOR^7$, or
—$CHR^6OCOOR^7$,
wherein $R^6$ is hydrogen or methyl and $R^7$ is $(C_1-C_6)$alkyl.

8. A cephem of claim 7 wherein R is 1-ethoxycarbonyloxyethyl.
9. A cephem of claim 7 wherein R is pivaloyloxymethyl.
10. The cephem of claim 9 wherein Y is

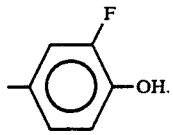

11. A pharmaceutical composition comprising an antibacterially effective amount of a compound of claim 1 and a pharmaceutically-acceptable carrier.
12. A pharmaceutical composition comprising an antibacterially effective amount of a compound of claim 2 and a pharmaceutically-acceptable carrier.
13. A pharmaceutically composition comprising an antibacterially effective amount of a compound of claim 7.
14. A method of treating a bacterial infection in a mammal which comprises treating said mammal with an antibacterially effective amount of a compound of claim 1.
15. A method of treating a bacterial infection in a mammal which comprises treating said mammal with an antibacterially effective amount of a compound of claim 2.
16. A method of treating a bacterial infection in a mammal which comprises treating said mammal with an antibacterially effective amount of a compound of claim 7.

* * * * *